US010611712B2

(12) United States Patent
Liao et al.

(10) Patent No.: US 10,611,712 B2
(45) Date of Patent: Apr. 7, 2020

(54) HYDROGENATION METHOD FOR PREPARING HYDROGENATED BISPHENOL-A HAVING A HIGHER TRANS/TRANS ISOMER RATIO

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Chia-Ruey Tsai, Taipei (TW); Sung-Chieh Chao, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 15/990,871

(22) Filed: May 29, 2018

(65) Prior Publication Data
US 2018/0346398 A1    Dec. 6, 2018

(30) Foreign Application Priority Data

May 31, 2017   (TW) .............................. 106117969 A

(51) Int. Cl.
*C07C 29/20*    (2006.01)
*B01J 23/46*    (2006.01)

(52) U.S. Cl.
CPC ............ *C07C 29/20* (2013.01); *B01J 23/462* (2013.01); *B01J 2219/00961* (2013.01); *B01J 2219/00963* (2013.01); *B01J 2219/00984* (2013.01); *C07C 2601/14* (2017.05)

(58) Field of Classification Search
None
See application file for complete search history.

(56) References Cited

U.S. PATENT DOCUMENTS

| 6,018,048 A    * | 1/2000 | Morikawa ................ B01J 25/00 546/185 |
| 6,248,924 B1 * | 6/2001 | Ruhl ........................ B01J 23/44 564/450 |
| 2012/0101238 A1* | 4/2012 | Fung .................... B01J 19/0066 525/523 |

* cited by examiner

*Primary Examiner* — Rosalynd A Keys
(74) *Attorney, Agent, or Firm* — Li & Cai Intellectual Property (USA) Office

(57) ABSTRACT

A hydrogenation method for preparing HBPA includes placing a BPA reaction liquid into a hydrogenation vessel with a hollow-shaft stirrer installed inside; starting the hollow-shaft stirrer to stir the BPA reaction liquid and simultaneously allowing hydrogen gas evenly distributed over and contact well with the BPA reaction liquid; in the presence of a single-metallic Ru/Al2O3 hydrogenation catalyst to proceed with a catalytic hydrogenation at low temperature and low pressure to produce HBPA, the HBPA has a yield of 99.7% or more, and particularly having a trans/trans isomer ratio above 63%.

6 Claims, 2 Drawing Sheets

HYDROGENATION METHOD FOR PREPARING HYDROGENATED BISPHENOL-A HAVING A HIGHER TRANS/TRANS ISOMER RATIO

BACKGROUND OF THE PRESENT INVENTION

1. Field of the Invention

The invention relates to a hydrogenation method for preparing hydrogenated bisphenol-A, and more particularly, to a hydrogenation method by using ruthenium/alumina (Ru/Al2O3) to prepare hydrogenated bisphenol-A having a higher trans/trans isomer ratio.

2. Description of Prior Art

Bisphenol-A (hereinafter referred to as BPA) has poor weatherability, under a severe environment, the benzene ring structure of BPA will cause BPA products to become yellowing and lead to limiting its outdoor application. In contrast, hydrogenated bisphenol-A (hereinafter referred to as HBPA) does not contain double bonds, has good weatherability, is not susceptible to yellowing, and has chemical stability, low viscosity as well as excellent processability. It has a wide range of applications and can be used to make epoxy, polycarbonate or unsaturated polyester resin, etc.

Additionally, it is well known that the trans, trans-isomer (or called trans/trans isomer) of HBPA is more valuable than its other cis, cis-isomer or cis, trans-isomer. It has been observed that reaction of the high-melting trans, trans isomer yields polymers having more symmetry and better physical properties, e.g., higher melting points.

In order to achieve different hydrogenation effects of HBPA, the prior art teaches different process for preparing HBPA, the key technology lies in the choice of active composition and carrier of the hydrogenation catalyst.

U.S. Pat. No. 4,503,273 introduces that hydrogenation of bisphenol-A was carried out using a supported nickel catalyst which had been pretreated with methanolic sodium hydroxide, and alumina is preferred as a support. Compared to the same hydrogenation using an untreated catalyst, significant improvements in selectivity and reaction time were noted. In one embodiment, by using a diethylene glycol dimethyl ether as a solvent, bisphenol-A is hydrogenated in the presence of an alkali-modified nickel/alumina (Ni/Al2O3) catalyst at a temperature of 200° C. and a pressure of 1,200 to 1,500 psig. Under conditions, the selectivity of HBPA is 93.4%, and the HBPA has a trans/trans isomers ratio of 45.7%.

U.S. Pat. No. 4,503,273 further teaches that trans/trans isomers ratio contained in HBPA is not influenced by reaction time, reaction temperature and reaction solvent.

U.S. Pat. No. 4,847,394 teaches bisphenol-A is hydrogenated in the presence of a ruthenium catalyst at 20° C.–60° C. and under a pressure above 100 bar. But, no teaching is disclosed regarding trans/trans isomers ratio contained in HBPA.

U.S. Pat. No. 6,248,924 teaches bisphenol-A in tetrahydrofuran (THF) is hydrogenated in the presence of a hydrogenation catalyst at 150° C. and under a pressure above 20 bar. The hydrogenation catalyst is selected from ruthenium or palladium and optionally at least one Group Ib, VIIb, or VIIIb metal to a suitable support. But, no teaching is disclosed regarding trans/trans isomers ratio contained in HBPA too.

A known double-metallic catalyst is used as a hydrogenation catalyst, whose structure is a kind of core-shell structure formed from a support as a core and two noble metals selected from palladium, ruthenium and rhodium covered onto the support as a shell.

Bisphenol-A is hydrogenated in the presence of the double-metallic catalyst at 165° C. and under a pressure of 78 bar. Under conditions, the produced HBPA has a trans/trans isomers ratio higher than 55%, which is superior to the performance by using single-metallic catalyst as a hydrogenation catalyst. However, the price of palladium and rhodium is more expensive, about ten times, than that of rhodium, and particularly, recycling of those noble metals used for double-metallic catalyst is more complicated and then increases burden of investment.

Another known multiple-metallic catalyst is used as a hydrogenation catalyst formed from rhodium, palladium, nickel and copper.

By using isopropyl alcohol as a solvent, bisphenol-A is hydrogenated in the presence of the multiple-metallic catalyst at 200° C. and under a pressure of 90-120 bar. Under conditions, the yield of HBPA is 99%, and the HBPA has a trans/trans isomers ratio of 51%.

U.S. Pat. No. 4,487,979 teaches unrefined HBPA was recrystallized from chloroform solvent for purification. The HBPA has a trans/trans isomers ratio up to 91.60%, but the recovery rate of HBPA is only 26%, resulted in that the investment amount is then increased.

In practical application, HBPA provided with more increasing of trans/trans isomers ratio can help the produced epoxy resin to have possession of much better high temperature resistance, anti-yellowing capacity and stability.

In hydrogenated reaction of benzene rings, rhodium (Rh) metal has higher activity than that of ruthenium (Ru) and palladium (Pd) metals have, but rhodium catalysts are more expensive. In addition to the economic considerations, the existing technology almost teaches use of expensive noble metals such as rhodium or palladium to form as a hydrogenation catalyst, or teaches use of ruthenium added with rhodium or palladium to form as a double metallic catalyst or a multiple-metallic catalyst.

However, in hydrogenated reaction of HBPA, the existing technology has never taught use of ruthenium alone as a single-metallic catalyst for use in production of HBPA, and the produced HBPA has a trans/trans isomers ratio higher than 50%.

Although ruthenium (Ru) is relatively inexpensive, a careful assessment whether ruthenium catalyst could be repeatedly serve as a hydrogenation catalyst for producing HBPA is necessary. Therefore, BPA is hydrogenated in the presence of the ruthenium catalyst, to observe whether the BPA has an excellent conversion rate and selectivity and whether the produced HBPA have a favorable yield is very important. More especially, under proper operating conditions, how to reduce costs per unit of ruthenium catalyst is still very important.

SUMMARY OF THE INVENTION

The present invention provides a hydrogenation method for preparing hydrogenated bisphenol-A by using a single-metallic Ru/Al2O3 hydrogenation catalyst as a hydrogenation catalyst instead of either a double-metallic catalyst or a multiple-metallic catalyst given known containing rhodium (Rh) and palladium (Pd) noble metals, which single-metallic Ru/Al2O3 hydrogenation catalyst is, not only having a high active ability for hydrogenation of benzene ring but also having a fast hydrogenation reaction rate as well as having a good recyclability, favorable to decrease hydrogenation catalyst usage and reduce hydrogenation reaction time; in practical application, the bisphenol-A (BPA) being hydrogenated in the presence of single-metallic Ru/Al2O3 is capably performed under a lower pressure and a lower temperature to produce hydrogenated bisphenol-A (HBPA) preferable to have a higher trans/trans isomers ratio. Therefore, the hydrogenation method of the present invention helps to reduce the investment cost and is so economically valuable.

The present invention further provides a hydrogenation method for preparing HBPA having a higher trans/trans isomers ratio, including using a hydrogenation vessel equipped with a hollow-shaft stirrer capable of extracting and exhausting hydrogen gas (H2) and stirring BPA reaction liquid, and, after the hollow-shaft stirrer is started to work, performing hydrogenation to the BPA reaction liquid in the presence of the single-metallic Ru/Al2O3 hydrogenation catalyst at a reaction temperature of 80-200° C. with a hydrogenation pressure of 10-100 bar. Under conditions, the yield of HBPA is greater than 99.7%, and particularly the HBPA has a trans/trans isomers ratio promoted to above 63%.

The present invention further provides a hydrogenation method for preparing HBPA having a higher trans/trans isomers ratio from BPA, and the hydrogenation method comprises the following steps:

a) preparing a hydrogenation vessel that is provided therein with a hollow-shaft stirrer capable of extracting and exhausting air and stirring;
b) placing a BPA reaction liquid containing 5-60 wt % of BPA reactant, based on the total weight of the BPA reaction liquid, into the hydrogenation vessel;
c) adding a single-metallic Ru/Al2O3 hydrogenation catalyst in an amount of 0.02-15.0 wt % based on the weight of BPA;
d) maintaining constant pressure after introducing a hydrogen gas with a pressure of 40-70 bar;
e) starting the hollow-shaft stirrer to stir the BPA reaction liquid via holding the pressure of step d) at room temperature for 10 minutes, then raising the temperature to 120 to 180° C., and being hydrogenated at this temperature for 10 to 20 hours; and
f) after the hydrogenated reaction is completed, cooling the reaction liquid to the room temperature, filtering out the catalyst and optionally further removing the solvent to obtain the produced HBPA which has a yield of greater than 99.7% as well as has a trans/trans isomers ratio promoted to above 63%.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE PREFERRED EMBODIMENTS

Figure 1:
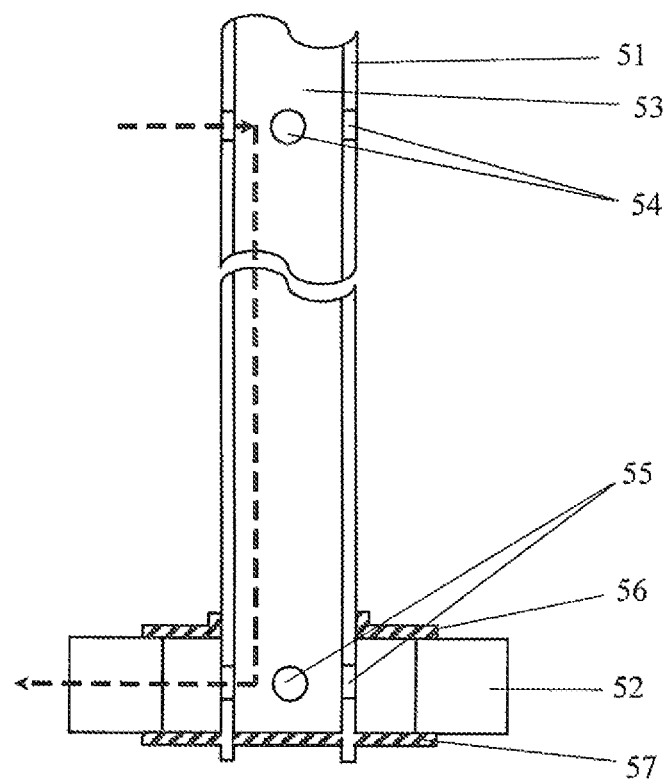
FIG. 1 is a longitudinal cross-sectional view of a hollow-shaft stirrer of the present invention having functions of extracting and exhausting air and stirring.
Figure 2:
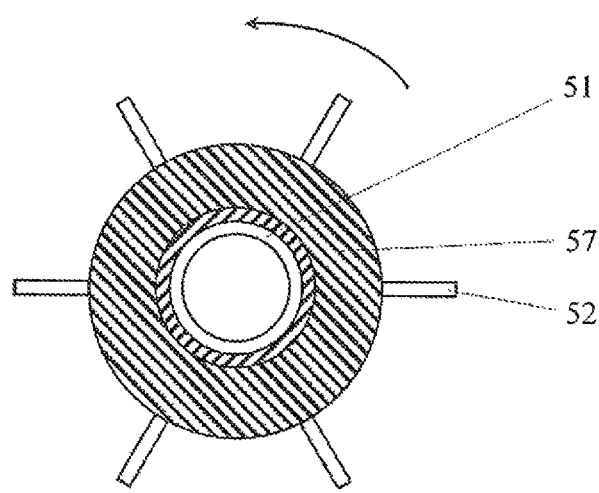
FIG. 2 is a top view of the hollow-shaft stirrer of FIG. 1.
Figure 3:
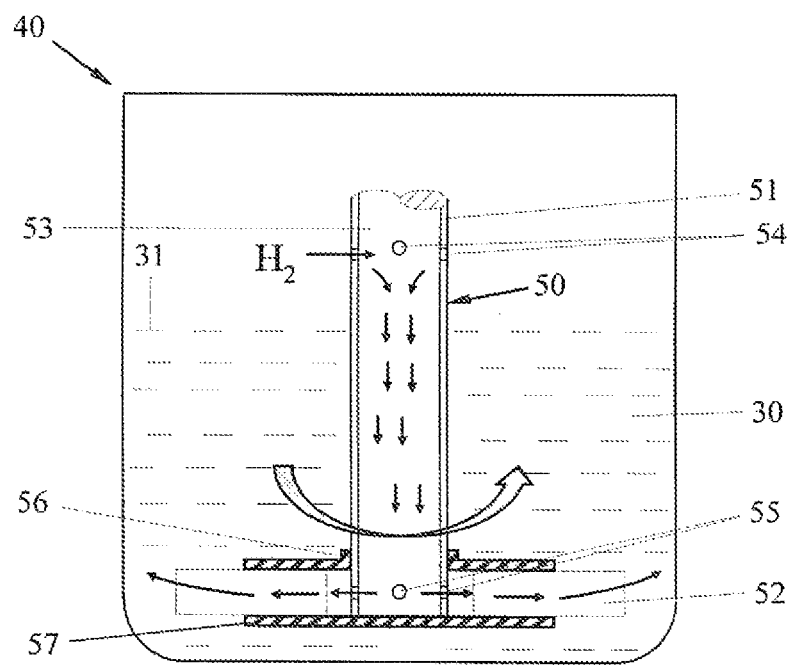
FIG. 3 is a schematic diagram to show a hydrogenation vessel for use in installation of the hollow-shaft stirrer of FIG. 1 inside and to proceed with hydrogenation reaction to produce HBPA under low pressure and low temperature.

Referring to FIGS. 1-3, as disclosed by the present invention, a hydrogenation vessel 40 is a drum-shaped, air-tight, high-pressure vessel, with a height/diameter ratio of 0.4-3.0, for use in hydrogenating bisphenol-A (BPA) reaction solution 30 into hydrogenated bisphenol-A (HBPA). According to the present invention, a HBPA made from a BPA may be hydrogenated in a batch, semi-batch, continuous basis.

In the hydrogenation vessel 40 of the present invention, there is a hollow-shaft stirrer 50, which is capable of extracting and exhausting air and stirring, for enhancing the activity of the hydrogenation catalyst and speeding up hydrogenation of the BPA reaction solution 30. Therefore, the hydrogenation vessel 40 of the present invention allows hydrogenation of the BPA reaction solution 30 to be performed under relatively low pressure and low temperature, while improving the yield of a HBPA made from the BPA reaction solution 30 through hydrogenation.

In the hydrogenation vessel 40 of the present invention, in addition to the hollow-shaft stirrer 50 installed inside, it is also possible to install a plate heat exchanger or a coil at a bottom of the hydrogenation vessel 40 to remove the heat generated during hydrogenation reaction and prevent heat accumulation.

Referring to FIGS. 1-3, the hollow-shaft stirrer 50 structurally comprises a gas-introducing rotatory shaft 51 and several impellers 52, and further comprises an upper fixture 56 and a lower fixture 57, after both respectively secured on the gas-introducing rotatory shaft 51, to accomplish each impeller 52 become attached to a terminal of the gas-introducing rotatory shaft 51.

The gas-introducing rotatory shaft 51 is internally formed as a gas channel 53, for delivering hydrogen gas. The gas-introducing rotatory shaft 51 at its upper part has several air-extracting holes 54 communicated with the gas channel 53. In use, the air-extracting holes 54 are located above a liquid surface 31 of the BPA reaction solution 30, so that the hydrogen gas can be drawn into the gas channel 53. The gas-introducing rotatory shaft 51 at its lower part further has several air-exhausting holes 55 also communicated with the gas channel 53, for allowing the hydrogen gas drawn into the gas channel 53 to be exhausted out from the air-exhausting holes 55.

The impellers 52 of the hollow-shaft stirrer 50 may be plate vanes, curved vanes or vanes with grooves.

The hydrogenation catalyst used for hydrogenating the BPA reaction solution 30 of the present invention is a ruthenium-based catalyst carried on aluminum oxide (hereinafter abbreviated as single-metallic Ru/Al2O3 hydrogenation catalyst) which is more competitive in respect of cost when compared to the palladium-based catalysts or the rhodium-based catalysts. This single-metallic Ru/Al2O3 hydrogenation catalyst has a high active ability for hydrogenation of benzene ring.

In the present invention, the single-metallic Ru/Al2O3 hydrogenation catalyst is used in an amount of preferably 0.02-15 wt %, or more preferably 0.05-10 wt %, based on the weight of the BPA reactants.

To prepare the BPA reaction solution 30, the BPA is directly dissolved in a liquid that has been contained in the hydrogenation vessel 40 of the present invention, or alternatively, the BPA is previously made into a solution with a solvent, before poured into the hydrogenation vessel 40 of the present invention.

When the BPA reaction liquid 30 is prepared, the solvent used is a lower alcohol or a higher alcohol, such as isopropanol, butanol or hexanol etc., and preferably isopropyl alcohol.

The amount of the BPA reactant contained in the BPA reaction liquid 30 is ranged from 5 wt % to 60 wt %, preferably ranged from 10 wt % to 50 wt %.

With the hollow-shaft stirrer 50 and the plate heat exchanger or coil pipe, the hydrogenation vessel 40 of the present invention facilitates increasing the yield of the HBPA made from the BPA through hydrogenation, the reason is that the hydrogen gas and the reaction liquid contact well in the hydrogenation vessel 40, and the heat generated during hydrogenation can be timely dissipated so that hydrogenation can be performed well under low pressure and low temperature.

Therefore, the reaction takes place in the hydrogenation vessel 40 of the present invention at 80-200° C., or preferably 120-180° C. or more preferably 165-180° C., with a pressure of the hydrogen gas at 10-100 bar, or preferably 40-80 bar or more preferably 40-70 bar, for 10 to 20 hours or preferably 14 to 20 hours.

Although the hydrogenation vessel 40 of the present invention as described uses pure hydrogen gas, it is to be appreciated that hydrogen gas containing inert gas is also useful for the purpose of the present invention. However, no matter pure hydrogen gas or hydrogen gas containing inert gas is used, it is important to avoid the gas containing sulfide or carbon monoxide that is harmful to the catalyst.

As shown in FIG. 3, for performing hydrogenation, the BPA reaction liquid 30 is poured into the disclosed hydrogenation vessel 40, with the single-metallic Ru/Al2O3 hydrogenation catalyst added in a proper amount and the hydrogen gas introduced. Then the hollow-shaft stirrer 50 is started. As the gas-introducing rotatory shaft 51 of the hollow-shaft stirrer 50 drives the impellers 52 to rotate and thereby stir the BPA reaction liquid 30, the hydrogen gas above the liquid surface 31 of the BPA reaction liquid 30 is drawn into the gas channel 53 of the gas-introducing rotatory shaft 51 through the air-extracting holes 54 of the gas-introducing rotatory shaft 51, and then exhausted from the air-exhausting holes 55 at the lower part of the gas-introducing rotatory shaft 51, where, with the assistance of the stir by the impellers 52, the exhaust hydrogen gas is evenly distributed over the reaction liquid 30, so as to improve the contact between the hydrogen gas and the BPA reaction liquid 30. Thereby, the reaction liquid 30 contains a high level of dissolved hydrogen, so the hydrogenation catalyst becomes more active to speed up hydrogenation.

According to the above description, the present invention discloses a hydrogenation method for preparing HBPA having a higher trans/trans isomers ratio from BPA, and the hydrogenation method comprises the following steps:

a) preparing a hydrogenation vessel 40 that is provided therein with a hollow-shaft stirrer 50 capable of extracting and exhausting air and stirring;

b) placing a BPA reaction liquid 30 containing 5-60 wt % of BPA reactant, based on the total weight of the BPA reaction liquid 30, into the hydrogenation vessel 40;

c) adding a single-metallic Ru/Al2O3 hydrogenation catalyst in an amount of 0.02-15.0 wt % based on the weight of BPA;

d) maintaining constant pressure after introducing a hydrogen gas with a pressure of 40-70 bar;

e) starting the hollow-shaft stirrer 50 to stir the BPA reaction liquid 30 via holding the pressure of step d) at room temperature for 10 minutes, then raising the temperature to 120 to 180° C., and being hydrogenated at this temperature for 10 to 20 hours; and f) after the hydrogenated reaction is completed, cooling the reaction liquid to the room temperature, filtering out the catalyst and optionally further removing the solvent to obtain the produced HBPA.

In addition to HBPA, the final product after completion of the hydrogenation reaction may contain unreacted BPA, solvents, impurities, catalysts, and catalyst derivatives. The composition of the final product, other than HBPA, generally contains 0-5 wt % of BPA, 5-50 wt % of HBPA, 55-60 wt % of solvent, 0.05-10 wt % of catalyst and 0-10 wt % of hydrogenolysis impurities.

By use of the hydrogenation vessel 40 equipped with a hollow-shaft stirrer 50 capable of extracting and exhausting air and stirring, the BPA reaction liquid 30 is hydrogenated in the presence of the single-metallic Ru/Al2O3 hydrogenation catalyst at a temperature of 80-200° C. with a pressure reduced to range between 10 bar and 100 bar. Under conditions, the yield of HBPA is greater than 99.7%, and particularly the HBPA has a trans/trans isomers ratio promoted to above 63%.

The following examples are provided to illustrate the present invention without limiting the scope of the present invention.

1. Conversion Rate Prediction in Percentage (%):

The conversion rate prediction in percentage (%) may be determined by dividing the difference obtained through S1 minus S2 by the S1.

Where, S1 is the concentration of BPA before hydrogenation reaction; and S2 is the concentration of BPA after hydrogenation reaction.

2. Selectivity Prediction in Percentage (%):

The selectivity prediction in percentage (%) may be determined by dividing the S3 by the difference obtained through S1 minus S2.

Where, S1 is the concentration of BPA before hydrogenation reaction; and S2 is the concentration of BPA after hydrogenation reaction, and S3 is the concentration of the produced HBPA after hydrogenation reaction.

3. Yield Prediction in Percentage (%):

The yield prediction in percentage (%) may be determined by dividing the S3 by the S1, where S1 is the concentration of BPA before hydrogenation reaction, and S3 is the concentration of the produced HBPA after hydrogenation reaction.

4. Percentage Ratio (%) of Trans/Trans Isomers:

The percentage ratio (%) of trans, trans-isomer content contained in the HBPA is the result of division of W1 by W2.

Where, by use of gas chromatography (GC) test, W1 is the integrated area of the trans, trans-isomer contained in the produced HBPA measured by GC test; and W2 is the integrated area of the produced HBPA measured by GC test.

Example 1

As shown in FIG. 3, 16 grams of Bisphenol-A (BPA) and 24 grams of isopropanol as a solvent are placed into a 100 mL high-pressure reaction tank with the disclosed hollow-shaft stirrer to form a reaction liquid. Ru/Al2O3 catalyst as a hydrogenation catalyst, whose structure is ruthenium-based catalyst carried on aluminum oxide, was added in 2 wt % by weight of the BPA.

Then hydrogen gas (H2) was introduced into the reaction tank up to a pressure of 70 bar where the pressure was maintained. The hollow-shaft stirrer in the reaction tank was started to drive its gas-introducing rotatory shaft being rotated at a stirring speed of 1,500 rpm. After at 25° C. of the room temperature to maintain the same stirring speed to stir the reaction liquid in the reaction tank for 10 minutes, the temperature of the reaction liquid in the reaction tank was increased to 180° C., where the hydrogenation reaction was performed for 20 hours.

After the reaction, the hydrogen gas was cut off and the hydrogen gas inside the reaction tank was exhausted. The reaction liquid was cooled to the room temperature. After having the catalyst filtered out, the reaction product was analyzed.

The results are shown in Table 1. The hydrogenation catalyst was used in an amount of 2 wt % based on the weight of BPA. The conversion rate of BPA was 100%, and the yield of HBPA was 99.8%. Particularly, the produced HBPA contains a high trans/trans isomers ratio, which is achieved up to 65.6%.

Example 2

The conditions were similar to Example 1, except that the reaction time for hydrogenation was from 20 hours reduced to 14 hours.

The results are shown in Table 1. The conversion rate of BPA was 100%, and the yield of HBPA was 99.7%. Particularly, the produced HBPA contains a higher trans/trans isomers ratio, which is achieved up to 65.5%.

Example 3

The conditions were similar to Example 1, except that the reaction time for hydrogenation was from 20 hours reduced to 10 hours.

The results are shown in Table 1. The conversion rate of BPA was 100%, and the yield of HBPA was 99.7%. Particularly, the produced HBPA contains a higher trans/trans isomers ratio, which is achieved up to 63.3%.

Comparative Example 1

The conditions were similar to Example 1, except that the reaction time for hydrogenation was from 20 hours reduced to 8 hours.

The results are shown in Table 1. The conversion rate of BPA was 100%, and the yield of HBPA was 94.8%. Nevertheless, the produced HBPA contain a relatively low trans/trans isomers ratio, which is only achieved to 49.0%.

Comparative Example 2

The conditions were similar to Example 1, except that the reaction time for hydrogenation was from 20 hours reduced to 3 hours.

The results are shown in Table 1. The conversion rate of BPA was 100%, and the yield of HBPA was 94.7%. Nevertheless, the produced HBPA contain a relatively low trans/trans isomers ratio, which is only achieved to 33.3%.

Comparative Example 3

The conditions were similar to Example 3, except that the reaction temperature for hydrogenation was 165° C. instead of 180° C.

The results are shown in Table 1. The conversion rate of BPA was 100%, and the yield of HBPA was 95.5%. Nevertheless, the produced HBPA contain a relatively low trans/trans isomers ratio, which is only achieved to 50.2%.

Comparative Example 4

The conditions were similar to Comparative Example 3, such as the reaction temperature for hydrogenation is still kept at same temperature of 165° C., except that the reaction time for hydrogenation was from 10 hours reduced to 3 hours.

The results are shown in Table 1. The conversion rate of BPA was 100%, and the yield of HBPA was 96.1%. Nevertheless, the produced HBPA contain a relatively low trans/trans isomers ratio, which is only achieved to 38.8%.

Comparative Example 5

The conditions were similar to Comparative Example 4, except that the reaction temperature for hydrogenation was 120° C. instead of 165° C.

The results are shown in Table 1. The conversion rate of BPA was 100%, and the yield of HBPA was 97.7%. Nevertheless, the produced HBPA contain a relatively low trans/trans isomers ratio, which is only achieved to 22.8%.

Comparative Example 6

The conditions were similar to Comparative Example 3, except that the Ru/Al2O3 hydrogenation catalyst used for hydrogenation reaction was, based on the weight of BPA, added in 0.7 wt % instead of 2 wt %.

The results are shown in Table 1. The conversion rate of BPA was 100%, and the yield of HBPA was 95.7%. Nevertheless, the produced HBPA contain a relatively low trans/trans isomers ratio, which is only achieved to 50.1%.

Comparative Example 7

The conditions were similar to Comparative Example 6, except that the Ru/Al2O3 hydrogenation catalyst used for hydrogenation reaction was, based on the weight of BPA, added in 0.2 wt % instead of 0.7 wt %.

The results are shown in Table 1. The conversion rate of BPA was 100%, and the yield of HBPA was 96.3%. Nevertheless, the produced HBPA contain a relatively low trans/trans isomers ratio, which is only achieved to 34.5%.

Comparative Example 8

The conditions were similar to Comparative Example 7, except that the reaction temperature for hydrogenation was ranged from 165° C. to 180° C., instead of 165° C.

The results are shown in Table 1. The conversion rate of BPA was 100%, and the yield of HBPA was 95.5%. Nevertheless, the produced HBPA contain a relatively low trans/trans isomers ratio, which is only achieved to 44.1%.

Comparative Example 9

The conditions were similar to Comparative Example 3, such as the reaction temperature for hydrogenation is still kept at same temperature of 165° C., except that the hydrogenation catalyst was changed to use Pd/Al2O3 hydrogenation catalyst instead of Ru/Al2O3 hydrogenation catalyst, and the reaction time for hydrogenation was required to prolong from 10 hours to 16 hours until the conversion rate of BPA was up to 100%.

The results are shown in Table 1. The conversion rate of BPA was 100%, and the yield of HBPA was 95.3%. Nevertheless, the produced HBPA contain a relatively low trans/trans isomers ratio, which is only achieved to 32.4%.

Comparative Example 10

The conditions were similar to Comparative Example 8, such as the reaction temperature for hydrogenation is still kept at same temperature of 180° C. and the Ru/Al2O3 hydrogenation catalyst was, based on the weight of BPA, still added in 0.2 wt %, except that the introducing pressure of hydrogen gas (H2) was 40 bar instead of 70 bar.

The results are shown in Table 1. The conversion rate of BPA was only 7.2%, and the yield of HBPA was only 6.8%. Nevertheless, the produced HBPA contain a relatively low trans/trans isomers ratio, which is only achieved to 24.4%.

Comparative Example 11

Figure 4:
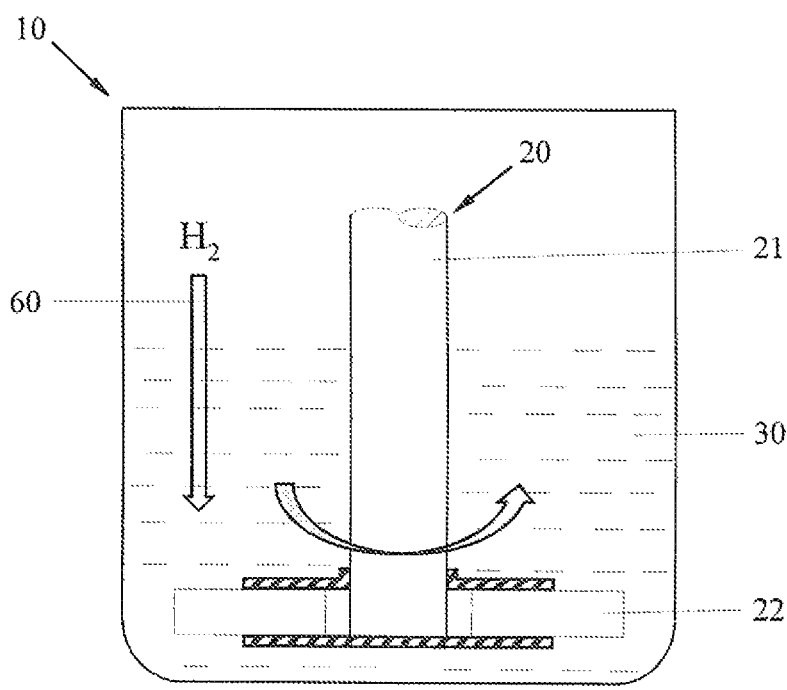
FIG. 4 is a schematic drawing of a conventional hydrogenation tank for operating under high pressure to produce HBPA.

This Comparative Example uses such a conventional hydrogenation reactor 10 illustrated in FIG. 4 for hydrogenation of BPA reaction solution 30, and the hydrogenation reactor 10 uses an impeller stirring device 20 installed inside, which is instead of the hollow-shaft stirrer 50 shown in FIG. 3 as well as taught by Examples 1 to 3. In addition to the impeller stirring device 20, a gas sprayer 60 is further used to be inserted into the BPA reaction liquid 30 in the hydrogenation reaction tank 10 to guide the hydrogen gas into the BPA reaction solution 30.

When the impeller stirring device 20 having a rotation shaft 21 is started to rotate, the blades 22 attached to a terminal of the rotation shaft 21 is begun stirring the BPA reaction solution 30, and through the gas sprayer 60 the hydrogen gas is forcibly guided and sprayed into the BPA reaction solution 30 to undergo a hydrogenation reaction.

The conditions were similar to Example 3, except that the conventional hydrogenation reactor 10 illustrated in FIG. 4 is used for hydrogenation reaction of the BPA reaction solution 30, the produced HBPA is then obtained.

The results are shown in Table 1. The hydrogenation catalyst was used in an amount of 2 wt % based on the weight of BPA. The conversion rate of BPA was 91.1%, and the yield of HBPA was 86.6%. Nevertheless, the produced HBPA contain a relatively low trans/trans isomers ratio, which is only achieved to 28.1%.

TABLE 1

By Hydrogenation of BPA; Yield and Trans/Trans Isomer Ratio of HBPA

| Item | | Example | | | Comparative Examples No. | | | | | | | | | | |
|---|---|---|---|---|---|---|---|---|---|---|---|---|---|---|---|
| | | 1 | 2 | 3 | 1 | 2 | 3 | 4 | 5 | 6 | 7 | 8 | 9 | 10 | 11 |
| Hydrogenation Vessel[1] | | v | v | v | v | v | v | v | v | v | v | v | v | v | — |
| Hydrogenation Reactor[2] | | — | — | — | — | — | — | — | — | — | — | — | — | — | v |
| Ru/Al2O3 Catalyst | | v | v | v | v | v | v | v | v | v | v | v | — | v | v |
| Pd/Al2O3 Catalyst | | — | — | — | — | — | — | — | — | — | — | — | v | — | — |
| Bisphenol-A (g) | | 16 | 16 | 16 | 16 | 16 | 16 | 16 | 16 | 16 | 16 | 16 | 16 | 16 | 16 |
| Isopropyl Alcohol (g) | | 24 | 24 | 24 | 24 | 24 | 24 | 24 | 24 | 24 | 24 | 24 | 24 | 24 | 24 |
| Usage of Catalyst (wt %) | | 2 | 2 | 2 | 2 | 2 | 2 | 2 | 2 | 0.7 | 0.2 | 0.2 | 2 | 0.2 | 2 |
| Pressure of H2 gas (bar) | | 70 | 70 | 70 | 70 | 70 | 70 | 70 | 70 | 70 | 70 | 70 | 70 | 40 | 70 |
| Temperature (° C.) | | 180 | 180 | 180 | 180 | 180 | 165 | 165 | 120 | 165 | 165 | 165-180 | 165 | 180 | 180 |
| Reaction Time (hours) | | 20 | 14 | 10 | 8 | 3 | 10 | 3 | 3 | 10 | 10 | 10 | 16 | 10 | 10 |
| Conversion Rate (%) | | 100 | 100 | 100 | 100 | 100 | 100 | 100 | 100 | 100 | 100 | 100 | 100 | 7.2 | 91.1 |
| Selectivity (%) | | 99.8 | 99.7 | 99.7 | 94.8 | 94.7 | 95.5 | 96.1 | 97.7 | 95.7 | 96.3 | 95.5 | 95.3 | 94.8 | 95.1 |
| Yield[3] (%) | | 99.8 | 99.7 | 99.7 | 94.8 | 94.7 | 95.5 | 96.1 | 97.7 | 95.7 | 96.3 | 95.5 | 95.3 | 6.8 | 86.6 |
| Isomer ratio | cis/cis (%) | 5.4 | 5.6 | 6.0 | 8.9 | 14 | 8.8 | 15.4 | 29.7 | 8.9 | 18.4 | 11.9 | 20.8 | 30.1 | 22.1 |
| | cis/trans (%) | 29.0 | 28.9 | 30.7 | 42.1 | 52.7 | 41 | 45.8 | 47.5 | 41 | 47.2 | 44 | 46.9 | 45.5 | 49.8 |
| | trans/trans (%) | 65.6 | 65.5 | 63.3 | 49.0 | 33.3 | 50.2 | 38.8 | 22.8 | 50.1 | 34.5 | 44.1 | 32.4 | 24.4 | 28.1 |

Note
[1]The hydrogenation vessel has at interior installed a hollow-shaft stirrer capable of extracting and exhausting H2 gas and stirring BPA reaction liquid.
Note
[2]The hydrogenation reactor is a conventional hydrogenation reactor without a hollow-shaft stirrer installed inside.
Note
[3]It represents for the yield of HBPA.

Result

1. As compared the Examples 1-3 with the Comparative Examples 1-2, under the same conditions except hydrogenation reaction time, the conversion rate of BPA was 100% after catalytic hydrogenation for 3 hours, but the reaction period of catalytic hydrogenation is from 3 hours extended to 10 hours, the produced HBPA has a trans/trans isomers ratio raised from 33.3% up to 63.3%. Particularly, the produced HBPA of Example 1 has a trans/trans isomers ratio raised to 65.6% after catalytic hydrogenation for 20 hours.

It obviously teaches the reaction period of catalytic hydrogenation is an important factor regarding to promote the produced HBPA has an improved higher trans/trans isomers ratio.

2. As compared the Example 3 with the Comparative Example 3, under the same conditions except catalytic hydrogenation temperature, the produced HBPA of Example 3 is hydrogenated at catalytic hydrogenation temperature of 180° C., not same that of 165° C. taught by the Comparative Example 3.

The produced HBPA of the Example 3 has a yield of 99.7%, and the HBPA has a trans/trans isomers ratio above 63.3%, all superior to that of the Comparative Example 3.

It obviously further teaches the catalytic hydrogenation reaction temperature is another important factor regarding to promote the produced HBPA has an improved higher yield and higher trans/trans isomers ratio.

3. Observing the test results of Comparative Examples 2, 4 and 5 from Table 1, as the reaction temperature increased from 120° C. to 165° C. and further from 165° C. to 180° C., the yield of HBPA gradually decreased to 94.7%. No matter the HBPA has increase of trans/trans isomers ratio, the amount of trans/trans isomers ratio was still only about 30%. The reason is that the catalytic hydrogenation reaction time less than 3 hours is not enough to produce the HBPA having a trans/trans isomers ratio above 50%.

It obviously teaches both the catalytic hydrogenation reaction time and temperature are important factors to produce the HBPA has an improved higher trans/trans isomers ratio.

4. Observing the test results of Comparative Examples 3, 6 and 7 from Table 1, as the usage of Ru/Al2O3 hydrogenation catalyst decreased from 2 wt % to 0.7 wt % and further from 0.7 wt % to 0.2 wt %, the yield of HBPA gradually increased to 96.3%, but the HBPA has decrease of trans/trans isomers ratio to about 34.5% or less.

Generally, usage of hydrogenation catalyst if increased is favorable to fast catalytic hydrogenation to help the benzene ring being undergone to have a high conversion rate and a high selectivity. However, Ru/Al2O3 hydrogenation catalyst used by the Comparative Example 3 is of 2 wt % which is greater than that of 0.7 wt % used by the Comparative Example 6, the trans/trans isomer ratio contained in each produced HBPA is not much changed, but the yield of HBPA produced by the Comparative Example 3 is of 95.5% which is slightly lower than that of 95.7% produced by the Comparative Example 6. The reason is that the usage of the Ru/Al2O3 hydrogenation catalyst exceeds the maximum limit, the chance of side reactions happened in catalytic hydrogenation is increased so that the selection rate of benzene ring is then decreased.

More specially, the hydrogenation vessel used by those Comparative Examples 3, 6 and 7 has installed inside a hollow-shaft stirrer to perform extracting and exhausting H2 gas and stirring BPA reaction liquid, resulting in that the hydrogen gas and the reaction liquid contact well to help the Ru/Al2O3 hydrogenation catalyst providing with much higher activity to fast catalytic hydrogenation. Such that the usage of hydrogenation catalyst can be reduced.

5. The hydrogenation catalyst used in Comparative Example 8 is obtained from repeatedly recovering the Ru/Al2O3 hydrogenation catalyst after used 12 times in Example 3; as a result, the recovering hydrogenation catalyst still has its own reactivity, such that the yield of HBPA produced by the Comparative Example 8 is of 95.5% which is competitive no matter lower than that of 99.7% produced by the Example 3.

However, the catalytic hydrogenation reaction temperature of the Comparative Example 8 is ranged between 165° C. and 180° C. unstably, not always maintained at 180° C., resulting in that the produced HBPA has slightly decrease of trans/trans isomers ratio to about 44.1%. Oppositely, the produced HBPA has a trans/trans isomers ratio maintained to above 50%, if the catalytic hydrogenation reaction temperature is always maintained at 180° C.

6. In the hydrogenation reaction, the use of a palladium metal catalyst generally gives a produced HBPA has a higher ratio of trans/trans isomers. As compared the Comparative Examples 3 with the Comparative Examples 9, under the same conditions except using different hydrogenation catalyst with same amount of 5 wt %, the HBPA produced in the presence of Ru/Al2O3 hydrogenation catalyst has a trans/trans isomers ratio higher than that of HBPA produced by using Pd/Al2O3 hydrogenation catalyst.

It teaches the Ru/Al2O3 hydrogenation catalyst having a high active ability for hydrogenation of benzene ring is favorable to promote the produced HBPA has an improved higher trans/trans isomers ratio.

7. As compared the Comparative Examples 10 with the Comparative Examples 8, the conversion rate of BPA is raised from 7.2% to 100%, when the catalytic hydrogenation is performed under a pressure of 40 bar and of 70 bar instead.

It teaches the catalytic hydrogenation is preferably performed under a pressure of 70 bar or more.

8. As compared the Examples 3 with the Comparative Examples 11, under the same conditions except that the Example 3 uses the hydrogenation vessel having a hollow-shaft stirrer installed inside as well as the Comparative Examples 11 does not have the hollow-shaft stirrer inside, the produced HBPA has a yield raised from 86.6% to 99.7% and has a trans/trans isomer ratio raised from 28.1% up to 63.3%.

What is claimed is:

1. A hydrogenation method for preparing HBPA having a higher trans/trans isomers ratio from BPA, comprising the steps of:

a) placing a BPA reaction liquid containing 5-60 wt % of BPA reactant, based on the total weight of the BPA reaction liquid, into a hydrogenation vessel provided therein with a hollow-shaft stirrer capable of extracting hydrogen gas and exhausting hydrogen gas into the BPA reaction liquid as well as stirring the BPA reaction liquid;

b) adding a single-metallic Ru/Al$_2$O$_3$ hydrogenation catalyst in an amount of 0.02-15.0 wt % based on the weight of BPA reactant;

c) maintaining constant pressure after introducing a hydrogen gas with a pressure of 70 bar;
d) starting the hollow-shaft stirrer to stir the BPA reaction liquid, then raising the temperature to 180° C., and undergoing a catalytic hydrogenation for 10 to 20 hours; and
e) after completion of the catalytic hydrogenation reaction, cooling the reaction liquid to the room temperature, filtering out the catalyst and optionally further removing the solvent to obtain a produced HBPA having a yield of 99.7% or more as well as having a trans/trans isomers ratio of above 63%.

2. The hydrogenation method as defined in claim 1, wherein the using amount of the single-metallic $Ru/Al_2O_3$ hydrogenation catalyst of step b) is of 0.05-10 wt % based on the weight of BPA reactant.

3. The hydrogenation method as defined in claim 1, wherein at step a) the BPA reaction liquid is contained of 10-50 wt % of BPA reactant.

4. The hydrogenation method as defined in claim 1, wherein at step d) the catalytic hydrogenation is undergone for 14 to 20 hours.

5. The hydrogenation method as defined in claim 1, wherein the hydrogenation vessel of step a) is further provided with a heat exchange plate or a coil pipe for dissipating hydrogenation heat.

6. The hydrogenation method as defined in claim 1, wherein the hydrogenation vessel of step a) is drum-shaped vessel having a ratio of height to diameter ranged between 0.4 and 3.0.

* * * * *